United States Patent [19]

Srinivasan

[11] Patent Number: 5,739,015
[45] Date of Patent: Apr. 14, 1998

[54] BIOTRANSFORMATION OF CHITIN TO CHITOSAN

[75] Inventor: Vadake R. Srinivasan, Baton Rouge, La.

[73] Assignee: Board of Supervisors of Louisiana State University and Agricultural and Mechanical College, Baton Rouge, La.

[21] Appl. No.: 815,282

[22] Filed: Mar. 10, 1997

[51] Int. Cl.$^6$ .............................. C12P 19/04; C12N 1/12; C13K 1/02
[52] U.S. Cl. ........................ 435/101; 435/252.1; 127/37
[58] Field of Search ................. 435/101, 252.1; 127/37

[56] References Cited

U.S. PATENT DOCUMENTS

| 4,195,175 | 3/1980 | Peniston et al. ........................ 536/20 |
| 5,232,842 | 8/1993 | Park et al. ............................ 435/101 |

OTHER PUBLICATIONS

Tsigos, et al., "Purification and Characterization of Chitin Deacetylase from *Collectotrichum Lindemuthianum*," The Journal of Biological Chemistry, vol. 270, No. 44, pp. 26286–26291 (1995).

*Primary Examiner*—Jean C. Witz
*Assistant Examiner*—Susan Hanley
*Attorney, Agent, or Firm*—John H. Runnels

[57] ABSTRACT

An *Alcaligenes* bacterium has been isolated from municipal sewage that contains a chitin deacetylase that can deacetylate chitin to chitosan.

4 Claims, No Drawings

BIOTRANSFORMATION OF CHITIN TO CHITOSAN

This invention pertains to a previously unknown bacterium capable of transforming chitin to the more soluble, useful product chitosan.

Chitin is one of the most abundant naturally occurring carbohydrates, second only to cellulose. Chitin is an insoluble, linear homopolymer of $\beta$-(1→4)-linked-N-acetyl-D-glucosamine. It is widely distributed in nature as a structural component of exoskeletons of crustaceans, insects, and other arthropods, as well as a component of the cell walls of most fungi and some algae.

Chitin can be easily extracted from shellfish waste, and hence is a readily renewable resource. However, chitin is extremely insoluble and has yet to find large-scale industrial uses. Chitin can be converted to chitosan without depolymerization by deacetylation. Chitosan, $\beta$-(1→4)-linked-D-glucosamine, is soluble in acid solutions, and has a wide range of uses: e.g., as a natural insecticide, a biopolymer for binding metals, or a base for cosmetics. At present, deacetylation of chitin to chitosan is usually achieved by thermochemical treatment of chitin to remove the acetyl groups without depolymerization. This process uses strong alkali at high temperatures for extended periods of time. See, e.g., U.S. Pat. No. 4,195,175. The process is energy-intensive and generates a pollutant stream of spent alkaline liquor.

Chitin deacetylase, an enzyme that catalyzes the conversion of chitin to chitosan by the deacetylation of N-acetyl-D-glucosamine residues, has been identified and purified from extracts of fungi. See U.S. Pat. No. 5,232,842; and Tsigos, et al., "Purification and Characterization of Chitin Deacetylase from *Collectotrichum lindemuthianum*," The Journal of Biological Chemistry, vol. 270, no. 44, pp. 26286–26291 (1995). Analogous enzymes, however, have not previously been identified in a bacterial species.

A previously unknown bacterium has been isolated from municipal sewage. This bacterium can deacetylate chitin to the more useful, soluble chitosan. Biotransformation of chitin to chitosan by bacteria can be used in an economical and environmentally-friendly process. Bacteria are easier and faster than fungi to grow in a large-scale fermentation system. Additionally, bacteria can be utilized without the necessity of purifying the enzyme.

A sample of sewage mixed liquor was obtained from the Baton Rouge Water Treatment facility at River Road, Baton Rouge, La. The sample was homogenized at low speed for 3 to 5 min in a Waring Blender and filtered through loosely packed gauze to remove large and filamentous particles. Ten ml of the sample was inoculated into a 500 ml Erlenmeyer flask with 100 ml of the following medium: 1 gm of yeast extract, 0.4 gm of ammonium sulfate, and 0.15 gm of potassium dihydrogen phosphate. Chitin (100 mg) was pulverized to a particle size less than 100 mesh and added to the medium. The culture was incubated on a shaker bath at 37° C. for three to four days. Ten ml of the culture was used as the inoculum for a fresh medium of the same composition. The serial transfers were repeated twice to enrich organisms growing in the presence of chitin, for a total of three passages. The organisms were then plated on agar plates containing the same medium, but without chitin. The culture was diluted to obtain approximately 100 to 150 isolated colonies per plate.

Two hundred individual colonies were screened for chitin deacetylase activity by the following assay, which is itself believed to be novel. First a diagnostic strip was prepared by dissolving 5 gm p-nitroacetanilide in 100 ml ethanol. Strips of Whatman #1 filter paper were immersed in the solution, removed, and air-dried. This was repeated thrice to impregnate the strips with a sufficient concentration of p-nitroacetanilide. The dried strips were then cut to a size of 5 cm×1.0 cm.

Test tubes containing 5 ml of pre-sterilized nutrient medium of the same composition as above, except without chitin, were inoculated with organisms from individual colonies. The cultures were incubated at 37° C. for two days. After two days of growth in test tubes, 2 ml aliquots were transferred to another set of test tubes containing the strips impregnated with p-nitroacetanilide and incubated for 12 to 24 hr. The development of a yellow color in the strip indicated the presence of deacetylase-containing organisms. The yellow color occurred as p-nitroacetanilide, a colorless compound, was deacetylated to p-nitraniline, a yellow compound. Without wishing to be bound by this theory, it is believed that because chitin is an insoluble substrate the organism must either secrete the deacetylase enzyme extracellularly or locate it in the periplasm. Thus, the filter paper impregnated with p-nitroacetanilide simulated chitin and acted as a substrate for the chitin deacetylase.

Three of 200 cultures tested positive. These positive colonies were further examined for the ability to deacetylate chitin. The colonies were transferred to agar slants for maintenance. Six 250 ml Erlenmeyer flasks containing 50 ml growth medium were prepared. Chitin (50 mg) was added to each of three flasks. Each strain was inoculated into two flasks—one with chitin and one without. After two days incubation, chitin (50 mg) was added to each of the flasks that did not previously contain chitin to serve as a control. The cultures were centrifuged at 12,000 g for 15 min. The precipitate contained a mixture of bacteria, chitin, and chitosan (if in fact chitin had been deacetylated). To each of the centrifuge tubes was added 10 ml of 0.1N NaOH. The contents were mixed thoroughly and autoclaved for 15 min. The tubes were then allowed to come to room temperature and centrifuged again at 12,000 g for 15 min. The supernatant was carefully removed. Most of the cells were solubilized during the alkaline treatment, and the pellet contained chitin, chitosan, and small amounts of cell debris. Then 10 ml of 0.2% acetic acid was added to the residue, and the tube was left on a shaker overnight at room temperature. The mixture was centrifuged again at 12,000 g for 15 min. The supernatant, which presumably contained chitosan, was collected, and the presence of chitosan was determined qualitatively and quantitatively by the following methods: (1) the formation of turbidity on neutralization with alkali, 1N NaOH; (2) infrared spectroscopy according to the method of Smith et al., "Applications of Microspectroscopy in the Near Infrared Region," Applied Spectroscopy, vol. 43, pp. 865–873 (1989); and (3) quantitative determination with ninhydrin according to the method of Curolto et al., Analytical Biochemistry, vol. 211, pp. 240–241 (1993). The isolation of chitin is easily achieved after collection of the acidified supernatant by neutralizing the supernatant, causing the chitosan to precipitate. Approximately 5 to 7% degradation of chitin occurred in each of the three chitin-containing cultures.

In another experiment, chitin was partially deacetylated chemically, and then reacetylated with tritiated acetic anhydride to form acetyl-tritiated chitin. Then lysates of the organism were incubated with the tritiated chitin overnight. Radioactivity was observed in solution by the next morning, indicating that chitin had been deacetylated by the lysate.

The bacteria can be used to degrade chitin in a large-scale fermentation procedure. In one such procedure, the organisms are maintained on agar slants in the growth medium described above. A loopful of organisms is inoculated into 50 ml of medium (previously autoclaved to remove contaminants) in a 250 ml Erlenmeyer flask and incubated at 37° C. with aeration for 24 hr. The contents of the flask are then transferred to 500 ml of fresh medium and grown for another 24 hrs. The culture serves as an inoculum for a scale-up of 5 L of culture. At this stage the organisms may be grown continuously in a stirred tank reactor as a batch culture, by fed-batch, or continuous cultivation depending on the amount of organisms required. Similarly, the fermentation can be scaled-up to larger reactors. The organisms are harvested and suspended in a dilute nutrient medium, sufficient to maintain the viability of the organisms. This suspension is used for the biotransformation of chitin. Chitin is packed in a small tower, and the suspension of organisms is percolated through the tower. As the organisms pass through the tower, chitin will be deacetylated to chitosan, which can then be isolated as described above. The flow-rate of the suspension and the duration of percolation may be altered to obtain a desired percentage of deacetylation. The organisms are used in such a process as an immobilized enzyme system for deacetylation. After such an operation the organisms may be used as a by-product single cell protein, or as a resource for the production of other compounds, including the deacetylase enzyme.

The organisms were characterized by generally accepted biochemical tests. The three different positive cultures originated from the same bacterium. The organism was tentatively identified as belonging to the genus Alcaligenes using *Bergey's Manual of Determinative Microbiology*, William & Wilkins (1974). The organism is a motile, Gram-negative rod about 1 to 1.5μ in length and 0.5μ in diameter. The organism tested positive for the presence of catalase, oxidase, gelatinase, and β-galactosidase. It tested negative for caseinase and amylase. The bacterium was able to metabolize nitrate, but not indole and urea. It did not ferment glucose, lactose, or sucrose, and did not oxidize glucose.

A sample of the bacterium was deposited under the Budapest Treaty with the American Type Culture Collection (ATCC), 12301 Parklawn Drive, Rockville, Md. 20852 on Feb. 19, 1997, and was assigned ATCC Accession No. 55938. This deposit was made pursuant to a contract between ATCC and the assignee of this patent application, Board of Supervisors of Louisiana State University and Agricultural and Mechanical College. The contract with ATCC provides for permanent and unrestricted availability of the bacterium to the public on the issuance of the US. patent describing and identifying the deposit or the publication or the laying open to the public of any U.S. or foreign patent application, whichever comes first, and for availability of the progeny of the bacterium to one determined by the U.S. Commissioner of Patents and Trademarks to be entitled thereto under pertinent statutes and regulations. The assignee of the present application has agreed that if the bacterium on deposit should die or be lost or destroyed when cultivated under suitable conditions, it will be promptly replaced on notification with a viable culture of the same bacterium.

In the specification and claims, a "pure culture" is a population of cells that is derived from a single cell (or a group of genetically identical cells) by cell division, and that is substantially free of deleterious, viable, contaminating microorganisms.

The complete disclosures of all references cited in this specification are hereby incorporated by reference. In the event of an otherwise irreconcilable conflict, however, the present specification shall control.

I claim:

1. A biologically pure culture of bacteria having all the identifying characteristics of Alcaligenes bacteria ATCC accession number 55938; or the progeny of said culture; wherein said culture or said progeny is capable of producing chitosan upon fermentation in an aqueous nutrient medium in the presence of chitin.

2. A process for full or partial deacetylation of chitin to chitosan, comprising contacting chitin with a biologically pure culture of bacteria having all the identifying characteristics of Alcaligenes bacteria ATCC accession number 55938; or contacting chitin with the progeny of such a culture; wherein the culture or the progeny is capable of producing chitosan upon fermentation in an aqueous nutrient medium in the presence of chitin.

3. The process of claim 2, wherein said contacting occurs in an aqueous nutrient medium.

4. The process of claim 2, wherein the deacetylation is achieved by selecting the time of contact between the bacteria and the chitin to produce a selected degree of deacetylation.

* * * * *